United States Patent [19]

Kubo et al.

[11] Patent Number: 4,709,045

[45] Date of Patent: Nov. 24, 1987

[54] PROCESS FOR PRODUCING 1,2-SUBSTITUTED IMIDAZOLINE COMPOUNDS

[75] Inventors: Makoto Kubo, Wakayama; Koshiro Sotoya; Kazuhiko Okabe, both of Naga, all of Japan

[73] Assignee: Kao Corporation, Tokyo, Japan

[21] Appl. No.: 871,651

[22] Filed: Jun. 6, 1986

[30] Foreign Application Priority Data

Jun. 19, 1985 [JP] Japan .................................. 60-133294

[51] Int. Cl.$^4$ ............................................ C07D 233/04
[52] U.S. Cl. ..................................................... 548/352
[58] Field of Search ......................................... 548/352

[56] References Cited

U.S. PATENT DOCUMENTS 3,555,041  1/1971  Katz ..................................... 548/352

Primary Examiner—Henry R. Jiles
Assistant Examiner—Robert C. Whittenbaugh
Attorney, Agent, or Firm—Flynn, Thiel, Boutell & Tanis

[57] ABSTRACT

A 1,2-substituted imidazoline compound having the formula (I):

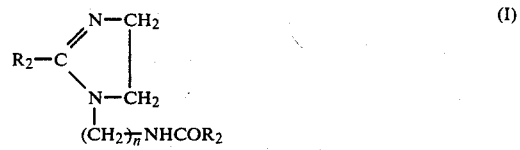

in which R2 is an alkyl or alkenyl group having 8 to 22 carbon atoms and n is 2 or 3, is produced by (1) feeding in a reactor a dialkylenetriamine (II) with a higher fatty acid of R2COOH or an ester thereof (III) at a molar ratio of the compound (III) to the compound (II) in the range of 1.5:1 to 1.8:1, (2) effecting the reaction at an internal temperature of 100° to 250° C. at a reduced pressure, (3) adding to the reaction mixture so that the above defined molar ratio in total may reach at least 2.0:1 and (4) continuing the reaction at an internal temperature of 100° to 250° C. at a reduced pressure. The reaction proceeds with a high yield of the product (I), without by-production to primary and second amines.

3 Claims, No Drawings

PROCESS FOR PRODUCING 1,2-SUBSTITUTED IMIDAZOLINE COMPOUNDS

The present invention relates to a two-step process for producing high-quality 1,2-substituted imidazoline compounds essentially free of primary and secondary amines from a dialkylenetriamine and a higher fatty acid or its ester.

It has been known that a quaternary ammonium salt of a compound having an imidazoline ring structure and an alkanoylaminoalkylene group in position 1 is effective as a textile softener. Some the textile softeners available on the market at present have such a structure. Such an imidazoline compound is produced by condensing a dialkylenetriamine having a secondary amino group in position γ with respect to at least one terminal primary amino group with a higher fatty acid. By using a suitable amount of the fatty acid in said condensation reaction, a corresponding diamidoamine is formed generally, which is then cyclized to form a given imidazoline structure. After the cyclization, the product is quaternizied with a quaternizing agent to form its quaternary ammonium salt. In conventional processes for producing imidazoline on an industrial scale, it is quite difficult to completely cyclize the intermediate amidoamine from the practical viewpoint. The maximum possible conversion in these processes is about 92% and, therefore, the cyclization product contains usually about 8% of primary and secondary amines.

It is impossible to quaternize these amines entirely by conventional quaternization processes and, as a result, these compounds are converted into amine salts and remain as impurities having no softening effect in the final product.

Though processes for producing 1,2-substituted imidazoline compounds are disclosed in the specifications of U.S. Pat. Nos. 2,355,837, 2,874,074 and 2,526,102, it has been found that, according to these processes, primary and secondary amines are formed in the abovementioned amounts in addition to the intended imidazoline compound. Therefore, in the subsequent quaternization step, undesirable amine salts are formed from these amines. Though a process for overcoming the above-described problem of the quality of a product by treating the primary and secondary amines with an alkoxylating agent and then converting them into a quaternary ammonium salt in the subsequent quaternization step is disclosed in the specification of U.S. Pat. No. 4,127,489, this process requires complicated steps and so is economically disadvantageous. Another disadvantage of this process is that a polymer of the alkoxylating agent is apt to contaminate the final product.

SUMMARY OF THE INVENTION

After intensive investigations made for the purpose of developing a process wherein only very small amounts of the primary and secondary amines are formed and, therefore, a high-quality imidazoline compound containing only small amounts of amine salts can be formed efficiently by a simple operation in the subsequent quaternization step by overcoming the above-mentioned defects of the conventional processes, the inventors have found that excellent results can be obtained by adding a higher fatty acid or its ester in two steps to a dialkyltriamine in a specified ratio. This fact has not been disclosed in any literature and any high-quality imidazoline compound could not be produced efficiently by a simple operation prior to the present invention which was developed by the inventors on the basis of the above fact.

The present invention provides a process for producing 1,2-substituted imidazoline compounds of the general formula (I):

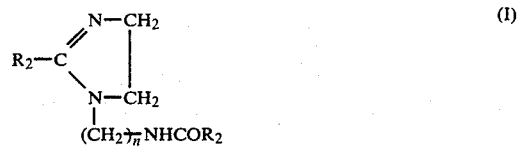

wherein $R_2$ represents an alkyl or alkenyl group having 8 to 22 carbon atoms and n represents an integer of 2 or 3,
by reacting a dialkylenetriamine of the general formula (II):

wherein $R_1$ represents an alkylene group having 2 or 3 carbon atoms,
with a higher fatty acid of the general formula (III):

wherein $R_2$ is as defined above,
or its ester, characterized by feeding the higher fatty acid of the general formula (III) or its ester and the dialkylenetriamine of the general formula (II) in such relative amounts that the molar ratio of the acyl group of the former to the dialkylenetriamine is in the range of 1.5 to 1.8/1, carrying out the reaction at an internal temperature of 100° to 250° C. under reduced pressure, adding the higher fatty acid or its ester to the reaction mixture so that the total molar ratio of the acyl group of the former to the dialkylenetriamine is at least 2.0/1, and continuing the reaction at an internal temperature of 100° to 250° C. under reduced pressure.

The invention may be defined as a process for producing a 1,2-substituted imidazoline compound having the formula (I):

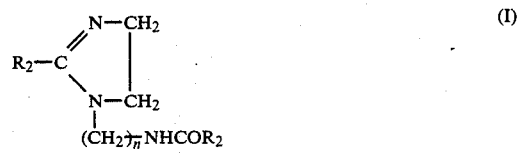

in which R2 is an alkyl or alkenyl group having 8 to 22 carbon atoms and n is 2 or 3, by (1) feeding in a reactor a dialkylenetriamine having the formula (II):

in which n is 2 or 3, with a higher fatty acid having the formula (III) or an ester thereof:

in which R2 is defined above, at a molar ratio of the compound (III) to the compound (II) in the range of 1.5:1 to 1.8:1, (2) effecting the reaction at an internal temperature of 100° to 250° C. at a reduced pressure, (3) adding to the reaction mixture so that the above defined molar ratio in total may reach at least 2.0:1 and (4) continuing the reaction at an internal temperature of 100° to 250° C. at a reduced pressure.

Now, the present invention will be described in detail. Examples of the dialkylenetriamines used in the process of the present invention include:

H$_2$N—CH$_2$CH$_2$—NH—CH$_2$CH$_2$—NH$_2$ and

N$_2$N—CH$_2$CH$_2$—NH—CH$_2$CH$_2$CH$_2$—NH$_2$

The higher fatty acids of the above general formula (III) include, for example, caprylic, capric, lauric, myristic, palmitic, stearic, oleic, nonadecanoic, behenic and erucic acids and their alkyl esters in which the alkyl has 1 to 4 carbon atoms, such as methyl and ethyl esters; mixtures of them derived from beef tallow or vegetable oils and their alkyl esters in which the alkyl has 1 to 4 carbon atoms, such as methyl and ethyl esters; and glycerides.

The relative amount of the higher fatty acid to one of the terminal primary amino groups and the secondary amino group in position γ is preferably small, namely, the molar ratio of the fatty acid to the dialkylenetriamine is preferably 1.5 to 1.8 in the reaction system in the first step.

The reaction conditions required of the reaction system include a temperature of 100° to 250° C., preferably 150° to 230° C., and a reduced pressure of preferably 1 to 50 mmHg, particularly 10 to 30 mmHg. The time required until the reaction reaches an equilibrium varies depending on the temperature, degree of the pressure reduction and variety of the fatty acid used. The time is at the longest 10 h and usually about 3 to 8 h. When diethylenetriamine is used as the dialkylenetriamine, the reaction in the first step can be shown as follows:

R$_2$COOH + NH$_2$CH$_2$CH$_2$NHCH$_2$CH$_2$NH$_2$    (A)

(used in an amount of 1.0 and 1.9 mol per mol of diethylenetriamine)

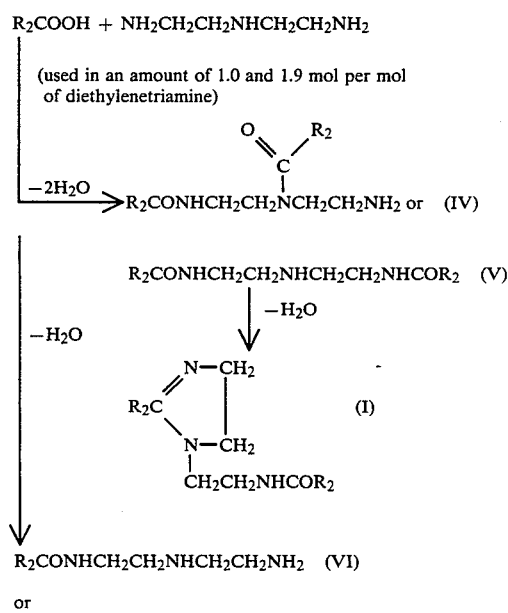

R$_2$CONHCH$_2$CH$_2$NHCH$_2$CH$_2$NH$_2$    (VI)

or

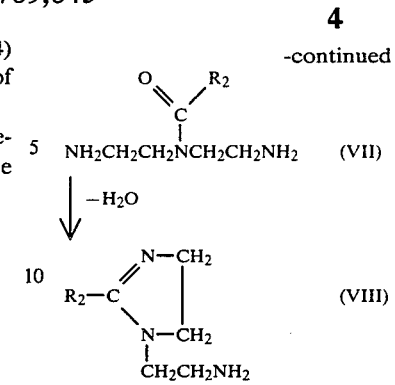

wherein R$_2$ is as defined above.

The inventors have found that the imidazoline mixture formed by the above-mentioned condensation in the first step comprises substantially a mixture of the intended 1-(2-alkanoylaminoethyl)-2-alkyl-2-imidazoline of the above general formula (I) and the 1-(2-aminoethyl)-2-alkyl-2-imidazoline of the above general formula (VIII) and that surprisingly, the amount of these imidazoline compounds exceeds 97% based on the whole imidazoline mixture composition.

The balance of the product comprises small amounts of the starting materials and the diamidoamine of the above general formula (IV) or (V).

When diethylenetriamine used as the dialkylenetriamine is reacted with the higher fatty acid in a molar ratio of the former to the latter of ½ under the above-mentioned condensation conditions according to a known condensation process other than that of the present invention, the amount of the imidazoline compound of the general formula (VIII) is about 2% and that of the intended imidazoline compound of the general formula (I) is about 86% based on the imidazoline mixture composition.

It is essential in the process of the present invention that the imidazoline compound of the general formula (VIII) must be formed in a given amount by controlling the above-mentioned molar ratio in the reaction system in the first stage.

For example, when the molar ratio of the higher fatty acid to diethylenetriamine used as the dialkylenetriamine is about 1.0 to 1.4, a major part of the formed imidazoline compounds comprises the compound of the above general formula (VIII). When the molar ratio of the higher fatty acid to diethylenetriamine is about 1.5 or higher, a major part of the formed imidazoline compounds comprises the imidazoline compound of the general formula (I).

The inventors have found that a molar ratio of the higher fatty acid to diethylenetriamine in the range of 1.5 to 1.8 brings about preferred results in the subsequent second step. When the molar ratio is not within said range, the imidazoline ring content is reduced or the amount of the primary and secondary amine components is increased inevitably in the subsequent second step.

The imidazoline compound of the above general formula (VIII) formed while the molar ratio is controlled in the given range is then acylated in the second step to form the intended imidazoline compound of the above general formula (I). This reaction is shown as follows:

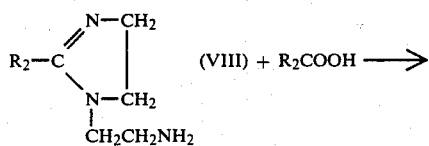

(VIII) + R₂COOH ⟶

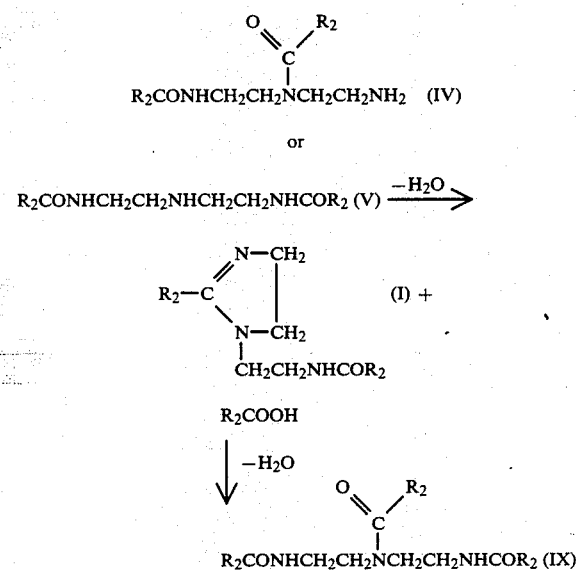

wherein $R_2$ is as defined above.

The reaction conditions required of the reaction system include a temperature of 100° to 250° C., preferably 150° to 230° C., and a reduced pressure of preferably 1 to 50 mmHg, particularly 10 to 30 mmHg. The time required until the reaction reaches an equilibrium varies depending on the temperature, degree of the pressure reduction and variety of the fatty acid used. The time is at the longest 10 h and usually about 3 to 8 h. Thus, the diamidoamine formed by the reaction in the first step is further cyclized or converted into a triamide.

The amount of the intended 1,2-substituted imidazoline compound obtained by the two-step operation reaches 95%. The balance of the product comprises small amounts of the starting fatty acid, the amide of the above general formula (IX) and very small amounts of the primary and secondary amines.

The mechanism of the formation of the intended high-quality product by the simple operation according to the process of the present invention unlike the conventional processes is supposedly as follows:

The inventors have found that the imidazoline compound of the above general formula (VIII) can be formed easily under the above-mentioned condensation conditions. Though such an imidazoline compound is essentially undesirable because it forms an amine salt in the quaterniziation step, the inventors noted easiness of the formation of the imidazoline compound and the reactivity of the alkyleneamino substituent in position 1 thereof. The present invention has been completed on the basis of this finding.

The molar ratio of the higher fatty acid to the dialkylenetriamine is important in the reaction system in the first step of the present invention. The inventors have found that when the molar ratio of the higher fatty acid to diethylenetriamine is in the range of 1.5 to 1.8, excellent results can be obtained in the subsequent second step.

When the molar ratio of the higher fatty acid to diethylenetriamine is not within said range, for example, when it is in the range of 1.0 to 1.4, the imidazoline ring content in the reaction system in the subsequent second step is reduced and it becomes difficult to obtain a high-quality 1,2-substituted imidazoline compound.

The inventors suppose that this phenomenon is related to the amount of water formed in the acylation of the imidazoline compound of the above general formula (VIII) in the second step.

When the imidazoline compound of the general formula (VIII) is present in a large amount, the amount of water formed in the acylation step is so much the larger. A part of water thus formed is reacted with the imidazoline compound to open the imidazoline ring. The intermediates of the above general formula (IV) or (V) formed by the reverse reaction are further dehydrated and cyclized or reacted with the higher fatty acid to form the compound of the general formula (IX). The inventors reached a conclusion that the conversion of the intermediate of the general formula (IV) or (V) into the compound of the general formula (IX) is easier than the cyclization thereof and, consequently, the imidazoline ring content is reduced.

When the molar ratio of the higher fatty acid to diethylenetriamine exceeds 1.8 beyond the range of the present invention, the amounts of the primary and secondary amines, particularly, the intermediate of the general formula (IV) or (V), are increased and the complete cyclization of the intermediate is difficult. As the result, 5 to 10 wt. % of the primary or secondary amine of the above general formula (IV) or (V) remains under the above-mentioned condensation conditions.

Effects of the Invention

Thus, according to the process of the present invention, the imidazoline compound can be produced easily from the dialkylenetriamine and the higher fatty acid or its ester, though production of this compound has been considered to be quite difficult. The operation in the process of the present invention is far simpler than that of the conventional processes. These are advantages obtained in carrying out the process of the present invention on an industrial scale.

The reaction product obtained by the process of the present invention has a high imidazoline compound content and an extremely low primary and secondary amine content and, therefore, the product can be used directly as a high-quality imidazoline compound for various purposes without resort to any after-treatment.

Examples

The following examples will further illustrate the present invention, which by no means limit the scope of the invention.

Test 1

400 g of beef tallow fatty acids (M.W.: 273) and 84.0 g of diethylenetriamine (hereinafter referred to as DETA, M.W.: 103.2) were placed in a 1 l four-necked flask provided with a stirrer, thermometer, sampling tube, condenser and pressure gauge. The molar ratio of the higher fatty acid to DETA was 1.8.

The flask was closed and the reaction was carried out at about 150° C. under a pressure of 400 mmHg for 3 h. Then, the temperature of the reaction system was elevated and the reaction was continued at 230° C. under 30 mmHg for 4 h. In the course of this reaction, the acid value was lowered to 1.6. The heating was stopped and the reaction mixture was cooled. The reaction product comprised 10.1 wt. % of 1-(2-aminoethyl)-2-tallowalkyl-2-imidazoline, 85.4 wt. % of 1-(2-tallowacylaminoethyl)-2-tallowalkyl-2-imidazoline, 3.7 wt. % of ditallowalkylamidoamine and 0.8 wt. % of the starting fatty acid. Then, 44.4 g of the beef tallow fatty acids (M.W.: 273) were added to the reaction product thus obtained. The molar ratio of the higher fatty acid to DETA was 0.2 in this stage. Then, the temperature of the reaction system was elevated and the reaction was carried out at 230° C. under 30 mmHg for 8 h. It was confirmed that the acid value was lowered to 2.4 and the reaction was terminated. The reaction product comprised 95 wt. % of 1-(2-tallowacylaminoethyl)-2-tallowalkyl-2-imidazoline, 1.0 wt. % of ditallowalkylamidoamine, 0.3 wt. % of 1-(2-aminoethyl)-2-tallowalkylimidazoline and 1.5 wt. % of the starting fatty acids.

Tests 2 to 6

The reaction was carried out in the same manner as in Test 1 except that a molar ratio of the beef tallow fatty acids (FA) to DETA in the reaction system was altered in the first and the second steps. The reaction conditions and the reaction products are shown in Table 1 together with the results of Test 1.

Tests 1 and 2 fall outside the scope of the invention, but Tests 3, 4 and 5 fall within it.

TABLE 1

| Test No. | 1 | 2 | 3 | 4 | 5 | 6 | 7 |
|---|---|---|---|---|---|---|---|
| FA/DETA molar ratio in the first step | 1.2 | 1.3 | 1.5 | 1.7 | 1.8 | 1.9 | |
| FA/DETA molar ratio in the second step | 0.8 | 0.7 | 0.5 | 0.3 | 0.2 | 0.1 | |
| Total molar ratio | 2.0 | 2.0 | 2.0 | 2.0 | 2.0 | 2.0 | 2.0 |
| Reaction products (wt. %) | | | | | | | |
| Primary and secondary amines (Note 1) | 0.8 | 0.9 | 0.7 | 1.0 | 1.3 | 5.3 | 9.8 |
| 1,2-Substituted imidazoline (Note 2) | 67.8 | 85.0 | 93.0 | 93.8 | 95.0 | 90.1 | 86.0 |
| Triamide | 24.6 | 11.0 | 3.0 | 2.8 | 2.2 | 1.9 | 5.0 |

(Note 1) Primary and secondary amines: monoalkylamide, dialkylamide and 1-(2-aminoethyl)-2-tallowalkyl-2-imidazoline
(Note 2) 1,2-substituted imidazoline: 1-(2-tallowacylaminoethyl)-2-tallowalkylimidazoline.

It is evident from data of Table 1 that in Tests 3, 4 and 5 according to the process of the present invention, a high imidazoline ring content and a low primary and secondary amine content were attained. On the other hand, when the reaction conditions were not within the range of the present invention, the imidazoline ring content was reduced or the amount of the primary and secondary amines was increased inevitably.

Test 7

444.4 g of beef tallow fatty acids (M.W.: 273) and 84.0 g of DETA (M.W.: 103.2) were placed in the same reactor as in Test 1. A molar ratio of the higher fatty acid to DETA was 2.0. The reactor was closed and the reaction was carried out at a temperature of about 150° C. under a pressure of 400 mmHg for 3 h. Then, the temperature of the reaction system was elevated and the reaction was continued at 230° C. under 30 mmHg for 4 h. It was confirmed that the acid value was lowered to 2.0 and the reaction was terminated. The results are shown in Table 1. Good results could not be obtained in this experiment in which the reaction was not divided into two steps.

The embodiments of the invention in which an exclusive property or privilege is claimed are defined as follows:

1. A process for producing a 1,2-substituted imidazoline compound having the formula (I):

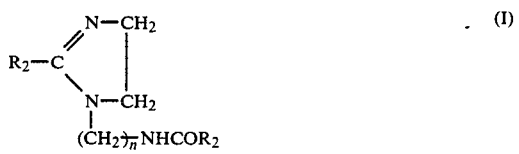

in which $R_2$ is alkyl or alkenyl having 8 to 22 carbon atoms and n is 2 or 3, which comprises (1) feeding into a reactor a dialkylenetriamine having the formula (II):

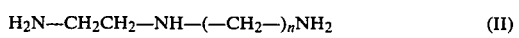

in which n is the same as defined above, and a higher fatty acid having the formula (III) or an ester thereof:

in which $R_2$ is the same as defined above, at a molar ratio of the compound (III) to the compound (II) in the range of 1.5:1 to 1.8:1, (2) effecting the reaction at an internal temperature of 100° to 250° C. at a reduced pressure until the reaction mixture consists essentially of a mixture of the compound (I) and the compound

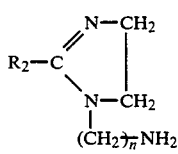

wherein $R_2$ and n have the same meanings as defined above, (3) then adding an additional amount of the compound (III) or ester thereof to the reaction mixture so that the molar ratio of III:II, based on the total amounts of III and II added to the reactor, is at least 2.0:1 and (4) continuing the reaction at an internal temperature of 100° to 250° C. at a reduced pressure until the reaction mixture consists essentially of compound I substantially free of primary and secondary amines.

2. A process as claimed in claim 1, in which the compound (II) is diethylenetriamine.

3. A process as claimed in claim 1, in which the first stage of the reaction (2) is conducted at a pressure of 1 to 50 mmHg for about 3 to 8 hours and the second stage of the reaction (4) is effected at a pressure of 1 to 50 mmHg for about 2 to 8 hours.

* * * * *